US00PP14036P39

(12) United States Plant Patent
Hall

(10) Patent No.: US PP14,036 P3
(45) Date of Patent: Jul. 29, 2003

(54) RASPBERRY VARIETY NAMED 'TADMOR'

(75) Inventor: Harvey K Hall, Motueka (NZ)

(73) Assignee: The Horticulture and Food Research Institute of New Zealand Limited, Palmerston North (NL)

( * ) Notice: Subject to any disclaimer, the term of this patent is extended or adjusted under 35 U.S.C. 154(b) by 243 days.

(21) Appl. No.: 09/866,444

(22) Filed: May 25, 2001

(65) Prior Publication Data

US 2002/0194654 P1 Dec. 19, 2002

(51) Int. Cl.[7] ..... A01H 5/00

(52) U.S. Cl. ..... Plt./204

(58) Field of Search ..... Plt./204

(56) References Cited

PUBLICATIONS

UPOV–ROM GTITM Computer Database, 2001/06, GTI Jouve Retrieval Software, citation for 'Tadmor'.*

New Zealand Plant Variety Rights Journal, No. 79, Jul.–Sep. 1997, Published: 14 Oct. 14, 1999, p. 2, item 6.

* cited by examiner

*Primary Examiner*—Bruce R. Campell
*Assistant Examiner*—Susan B. McCormick
(74) *Attorney, Agent, or Firm*—Greenlee, Winner and Sullivan, P.C.

(57) ABSTRACT

A new and distinct floricane fruiting variety of red raspberry (*Rubus idaeus* L.), named 'Tadmor' is described. The variety produces high yields of attractive, uniform sized, large, high flavored, bright red berries. The plant exhibits a semi spine-free spreading growth habit of greater vigor than other similar varieties. The fruit are suitable for consumption as high grade fresh berries and are also amenable to processing. In addition, the plant has displayed resistance to Raspberry Bushy Dwarf Virus (RBDV) under New Zealand conditions.

4 Drawing Sheets

Genus and species of plant claimed: *Rubus idaeus.*

BACKGROUND OF THE INVENTION

The new variety of red raspberry, *Rubus idaeus* L, was created in the course of a planned breeding program carried out at HortResearch Nelson, New Zealand. The parents used to make the cross in 1990 were the selections ORUS 576-47 (seed parent) and 86105N4.4 (pollen parent). The selection ORUS 576-47, since named 'Lewis' (not patented) originated from the Oregon State University, United States Department of Agriculture, Agriculture Research Service Rubus breeding program. 86105N4.4, since named 'Waimea' (not patented), is a RBDV resistant New Zealand selection.

The parentage of the new variety includes the Scottish varieties 'Glen Prosen' (not patented) and 'Glen Moy' (not patented), and the United States varieties 'Meeker' (not patented) and 'Willamette' (not patented). The background of 'Tadmor' also includes the species *Rubus pileatus* and *R. occidentalis* via the Scottish breeding program, and the species *R. strigosus* via the Oregon Rubus breeding program.

Seed from these crosses was grown and the original plant of the new variety was selected during the 1993–94 summer (Southern Hemisphere) and was found to exhibit:

(a) a semi spine-free arching growth habit of outstanding vigor, (b) the ability to form attractive, even sized large red fruit of good flavor in exceptionally high yields on medium-long fruiting laterals, and (c) resistance Raspberry Bushy Dwarf Virus (RBDV).

The new variety was first asexually propagated in 1994, reproduced by vegetative cuttings arising from root cuttings. Cuttings developed in spring in this way root within a 3–4 week propagation period, plants suitable for field planting are then generally ready in autumn of the same year. The resulting plants propagated true to type demonstrating that the characteristics of the new variety are stable and are transmitted without change through succeeding generations.

SUMMARY OF THE INVENTION

The new variety was tested and evaluated during the years 1995 to 2000 at HortResearch Nelson.

When compared to the parent 'Lewis', the new variety is found to form larger, similarly firm fruit in higher yields. 'Tadmor' is further distinguished from 'Lewis' by having more canes that are thicker and longer, and producing fruit which are lighter in color, with increased shininess and requiring greater force to separate the berry from the plug. When compared to the parent 'Waimea', the new variety exhibits larger, richer red colored fruit in higher yields, a later picking date (approximately 7 to 8 days later), and a longer picking period. 'Tadmor' is further distinguished from 'Waimea' by having a few spines on mature canes and many spines on juvenile canes, greater cane vigor and cane number, and by having fruit which are more difficult to separate the berry from the plug. Data collected during the evaluation period comparing fruiting performance of the new variety with standard New Zealand varieties is presented in Table 1.

TABLE 1

Comparison of fruiting performance.

| Variety | Average Yield (T/ha) | Berry Weight (g) |
|---|---|---|
| 'Tadmor' | 25.3 | 4.6 |
| 'Marcy' | 21.1 | 2.8 |
| 'Skeena' | 15.8 | 3.3 |

TABLE 1-continued

Comparison of fruiting performance.

| Variety | Average Yield (T/ha) | Berry Weight (g) |
|---|---|---|
| 'Chilliwack' | 15.0 | 2.9 |
| 'Waimea' | 22.3 | 3.3 |

The data presented in Table 1 demonstrate the exceptionally high fruit yield potential of the new variety, in particular, the greater individual berry weight of fruit of the new variety. 'Tadmor' berries commonly weigh approximately 4.6 g, with this fruit weight achieved consistently throughout the harvest season. Berries of the new variety are suitable for consumption as high-grade fresh fruit and also are well suited for processing. The color of the processed product is a lighter red than that of 'Marcy', 'Meeker', 'Skeena' or 'Willamette', standard varieties for processing in New Zealand or the United States.

BRIEF DESCRIPTION OF THE DRAWINGS

The accompanying photographs show typical specimens of the new variety in color as true as is reasonably possible. The photographs were prepared in December 2000 and depict three year-old plants and plant parts grown outdoors at HortResearch Nelson, New Zealand.

DETAILED DESCRIPTION

Figure 1:
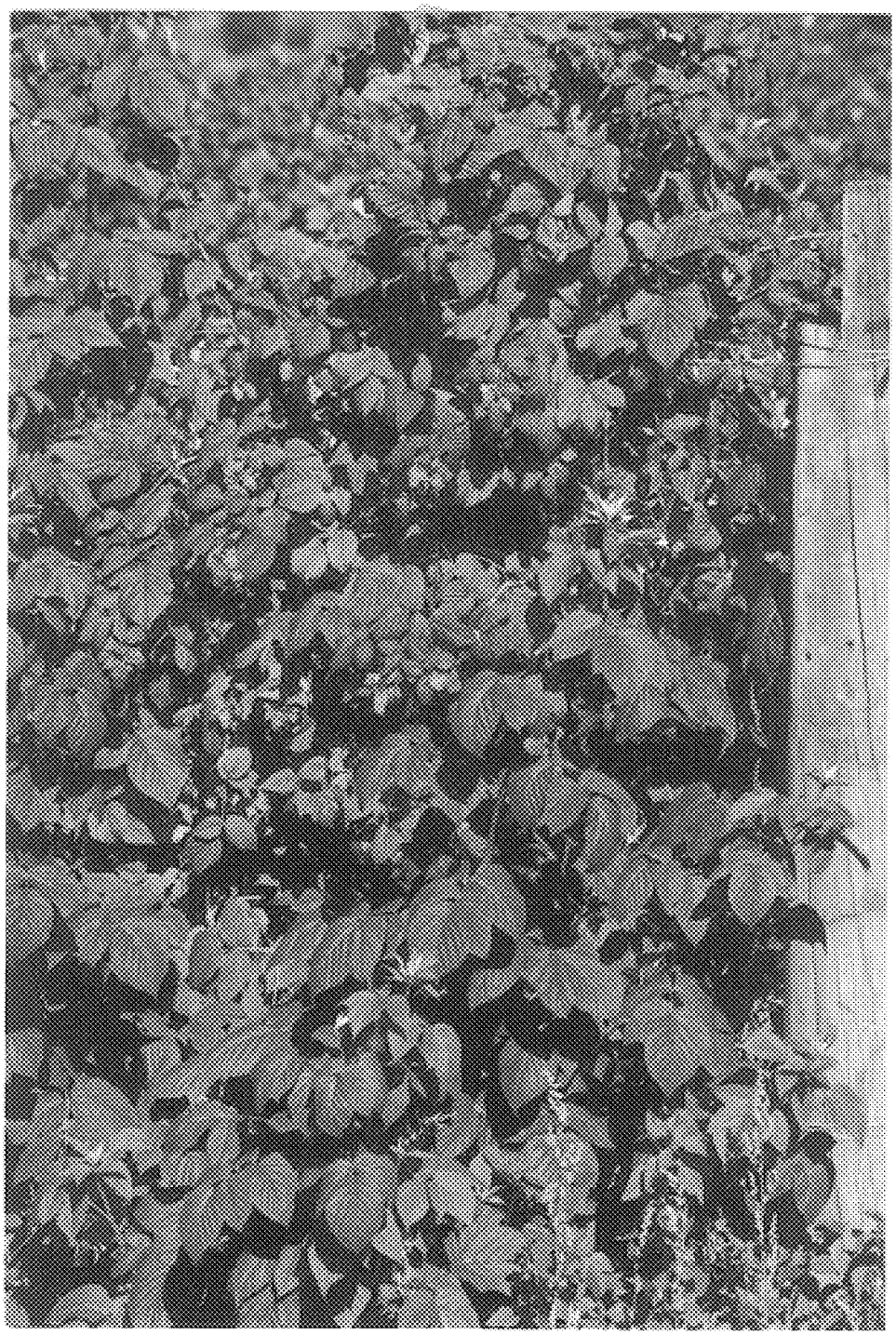
FIG. 1 illustrates a fruiting plant of the variety showing the large fruit size and high productivity. The fruiting laterals are shown to be medium length and slightly ascending.

Horticultural terminology is used in accordance with UPOV guidelines for raspberry. All dimensions are in millimeters, weights in grams (unless otherwise stated). Where a color reference is given, these refer to The R.H.S. Color Chart, The Royal Horticultural Society, London, $4^{th}$ Edition, 2001.

The specimens described were grown at HortResearch Nelson, New Zealand, and the plants were 2 years old in the 2000–2001 season when the observations were made. The plants were managed under practices to a standard considered reasonably acceptable in the horticultural industry. Environmental data for the growing area demonstrate conditions in spring and early summer (equating to the harvest period for the variety) as follows:

Spring (September/October); mean daily temperature in the range 10–12° C. (mean daily minimum 5.8° C., mean daily maximum 16.5° C.

Early summer (December/January); mean daily temperature 16.8° C. (mean daily minimum 11.1° C., mean daily maximum 22.4° C.

A cool temperate area, frost conditions are typically experienced in winter, with the lowest winter temperature unlikely to be colder than −10° C. Average annual rainfall is approximately 1125 mm.

Plant and foliage

Figure 2:
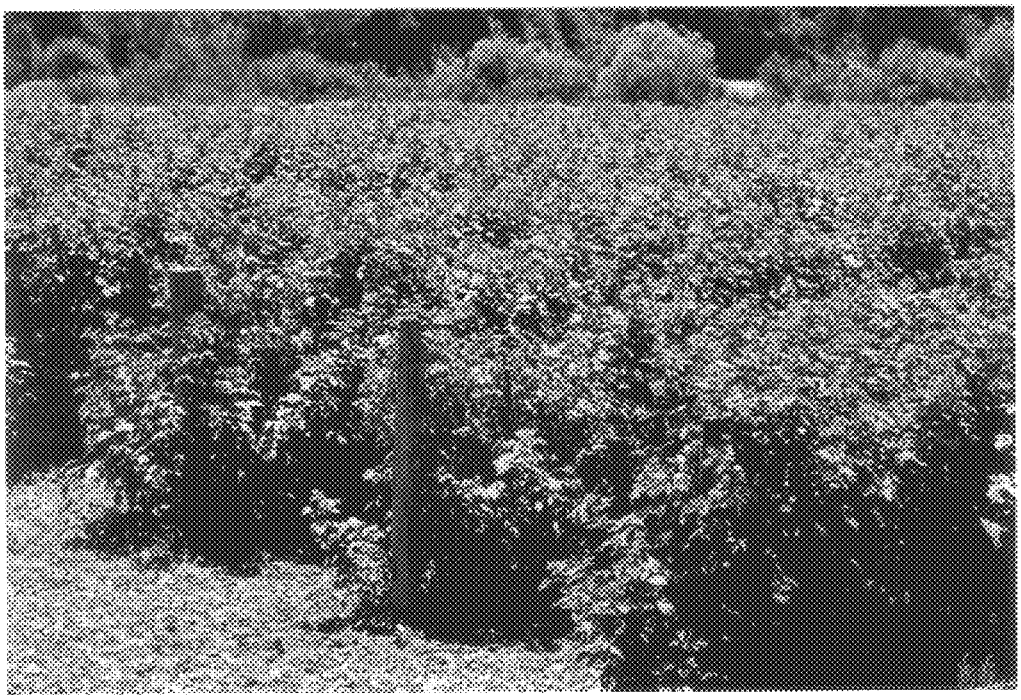
FIG. 2 illustrates typical plants of the variety showing the spreading nature of the canes at full canopy development.
Figure 4:
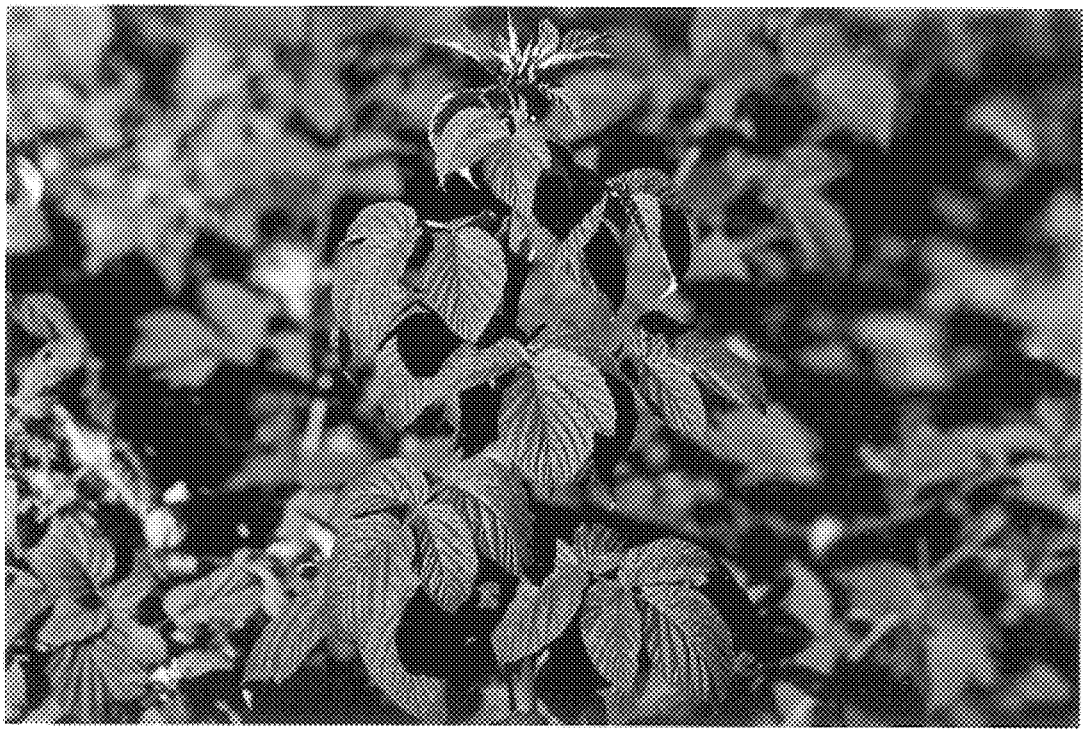
FIG. 4 illustrates a tip of growing foliage of the variety from a primocane with the leaflets at various stages of development.
Figure 5:
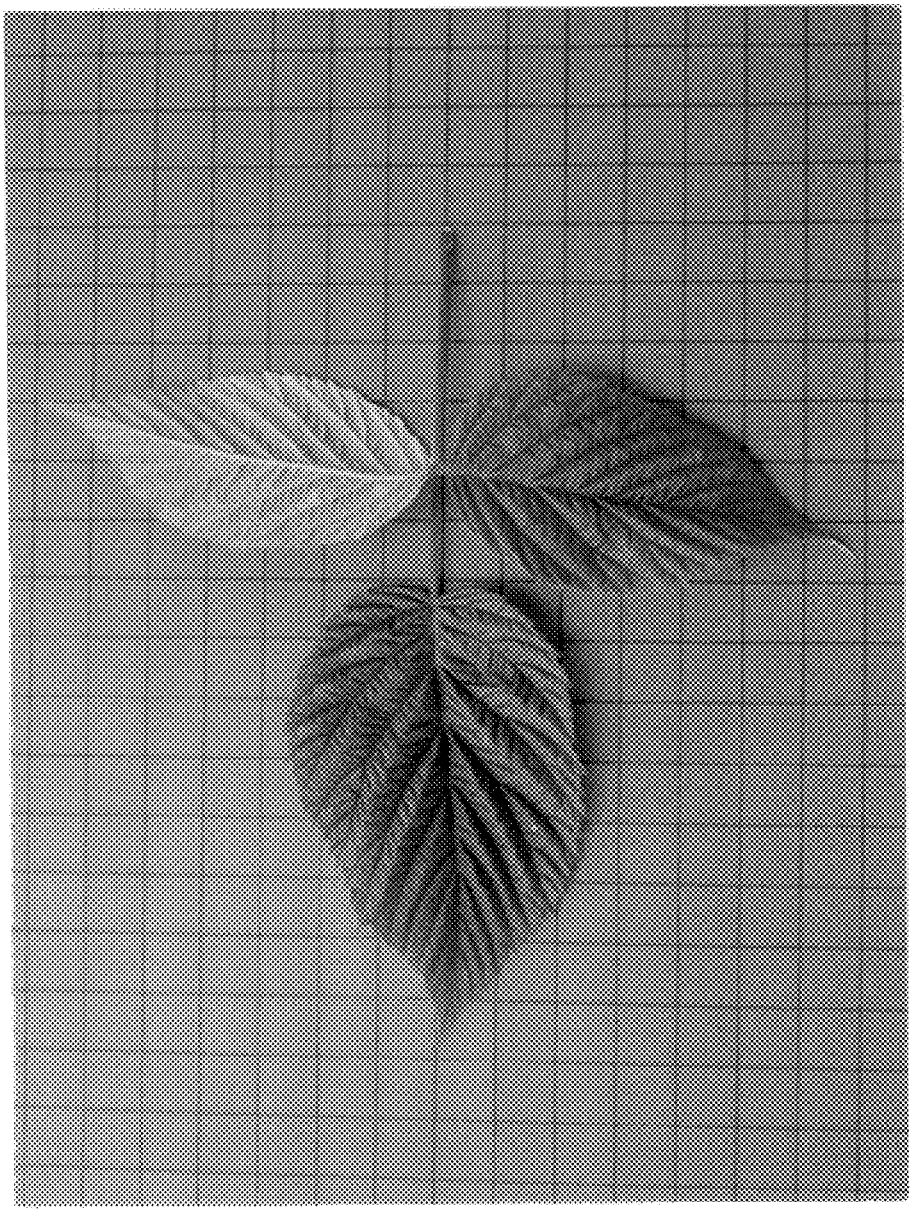
FIG. 5 illustrates fully opened leaflets of the variety from a floricane showing the upper and lower surface of the leaves.

The plant exhibits a spreading growth habit (FIG. 2). Typical mature plants range between 2000 mm to 2500 mm in height, although this may vary with the growing conditions. Very strong vigor is exhibited, manifested as a greater number of canes and longer, thicker canes than similar varieties. Cane length typically averages 2300 mm, however may be as long as 2700 mm. Internode length is typically in the range 80–90 mm. Spines (prickles/thorns) are largely absent on mature canes but frequently present on juvenile canes. Spines are near Purple N79B in color. New shoots commonly possess strong anthocyanin coloration, while mature canes display red coloration in summer and tan coloration (near Greyed-orange 175A) during the winter. Some purple coloration (near Purple N77A) is also evident on the upper portion of the cane in winter, the degree of coloration varying plant to plant. The fruit is borne primarily on the previous year's growth. The fruiting laterals are typically in a spreading attitude. The canes have a somewhat sparse leaf presentation that tends to provide excellent fruit presentation at harvest time. The leaves are compound, crinkled, almost flat, and moderately glossy (FIGS. 4 and 5).

The shape of the leaf apex is pointed while the general shape of the base is rounded, although some are weakly cordate. The leaf margin is moderately serrate. The mature leaf averages approximately 98.0 mm in length and averages approximately 72.0 mm in width. The venation pattern is wavy with pronounced veins, and there is moderate ridging between the veins. The leaves are green in coloration; the upper side being near Green 137A and the lower side being near Greyed-green 191B. The venation on the upper surface is the same color as the leaf, while the venation on the lower surface varies slightly from the leaf color (near Greyed-green 193A). The petiole averages approximately 66.3 mm in length and 1.6 mm in diameter, and is near Yellow-green 144A in color, with some anthocyanin coloration observed (near Red-purple 59A).

Inflorescence

White flowers are borne on short slender pedicels that have few spines (thorns/prickles). The time of bloom is late-season for a summer-fruiting raspberry. At HortResearch Nelson, the typical date bud burst commences is September $10^{th}$, with fifty percent of buds burst by early October (October $8^{th}$). The flowers have five sepals. These are near Green 139D in color and measure approximately 5.5 mm in length from base to tip. Typically there are five petals, elongated ovate in shape with a rounded apex and flat base. The petals average approximately 6.5 mm in length and 3.1 mm in width. They are typically smooth with some venation, have a smooth margin and are near White 155C in color. The pedicel is near Yellow-green 144A in color and averages 0.83 mm in diameter and 20 mm in length (observed range approximately 20 to 40 mm). However, the more basal the pedicel the longer it commonly becomes with pedicel lengths up to about 60 mm then being observed. A typical flower diameter is approximately 28 mm (from sepal tip to sepal tip i.e. the widest part of the flower). The flowers are predominantly borne singly, although sometimes in clusters of two or more. Terminal branch flower clusters frequently consist of two flowers and basal flower clusters may number three to five. The flowers have no discernible fragrance. The reproductive organs are typical for flowers of *Rubus idaeus* L.; the stigmas average approximately 7.00 mm in length and are near Green-white 157A in color; there are approximately 100–110 anthers, these being near Green-white 157B in color; the filaments averaging approximately 4.5 mm in length and being near White 155A in color.

Harvest

At HortResearch Nelson, the typical start date for picking the new variety is December $17^{th}$. Fifty 50 percent of the harvest is typically completed by January 5th and harvest ceases approximately February $4^{th}$. The date at which 50 percent of harvest is complete is approximately 20 days later for 'Tadmor' than for 'Marcy'. However, the duration of the harvest period for 'Tadmor' is similar to 'Marcy'.

'Tadmor' is moderately suitable for harvest by machine due to the moderate ease of removal of the berry from the plug. The fruit sample picked by this method is good quality but it may contain some over-ripe fruit that have not been removed the previous pick. After the passage of the machine, there is some fruit retained on the plant even if the plant is shaken more vigorously than is usual with 'Skeena', the standard for machine harvest in New Zealand as fruit are harder to remove.

Fruit

Figure 3:
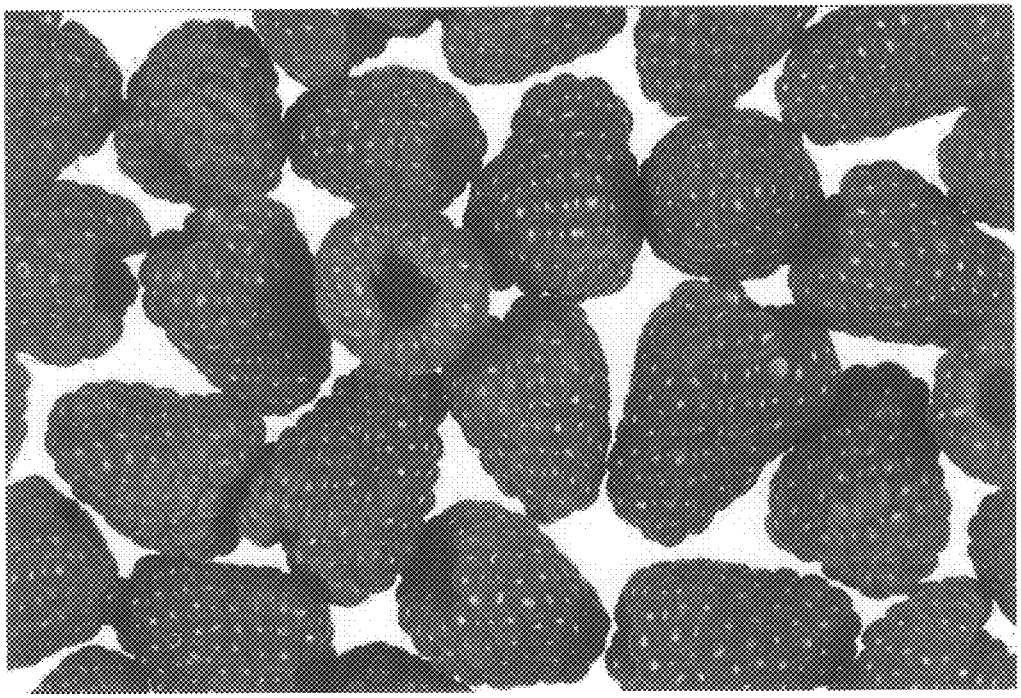
FIG. 3 illustrates enlarged close-up side and end views of typical fruit of the variety.

The berries formed on 'Tadmor' are large in size, similar in size to the variety 'Glen Ample' (U.S. Plant Pat. No. 11,418), and are typically much longer than broad: averaging approximately 26.0 mm in length and 22.0 mm in diameter. Average weight of berries produced at HortResearch Nelson during the 1999–2000 summer was 4.6 g. The fruit is round-conical in configuration (FIG. 3) and is bright red in appearance similar in color to the variety 'Malling Delight' (not patented) (external color near Red 53A, internal color near Red 46A) with a medium to high level of glossiness. The berries are firm and fleshy and of good flavor. The number of drupelets per fruit is commonly approximately 104 and seed weight typically ranges approximately 1.5 mg to 2.0 mg. The seeds average approximately 2.7 mm in length and 0.9 mm in diameter, and are near Greyed-orange 165D in color when dry.

In shelf life trials 'Tadmor' performs better than 'Marcy' and 'Skeena'. 'Tadmor' fruit has a better appearance than that of either of these varieties in commerial packs due to the larger, firmer fruit and light, bright color of the berries.

Pest and disease resistance

No data is available on resistance to aphids but 'Tadmor' has shown susceptibility to European red mites.

Since the selection of this clone in 1993 numerous tests for raspberry bushy dwarf virus (RBDV) have been done using ELISA but on no occasion has the virus been detected in spite of high infection pressure. From this we suggest that 'Tadmor' is likely to be resistant to the common strain of RBDV found in New Zealand.

Cultivation

'Tadmor' performs well in the cool temperate climate of the Nelson region under standard management practices for commercial raspberry production. A conservative approach to fertiliser applications is recommended, as overly generous applications may promote excessive cane growth due to the nature of the vigor of the plant.

I claim:

1. A new and distinct variety of raspberry plant, *Rubus idaeus* L, substantially as herein shown and described.

* * * * *